United States Patent [19]

Kim et al.

[11] Patent Number: 5,142,041
[45] Date of Patent: Aug. 25, 1992

[54] CEPHALOSPORIN INTERMEDIATES

[75] Inventors: Yong Z. Kim; Jae H. Yeo; Jong C. Lim; Won S. Kim; Chan S. Bang, all of Doryong, Rep. of Korea

[73] Assignee: Lucky, Ltd., Seoul, Rep. of Korea

[21] Appl. No.: 673,673

[22] Filed: Mar. 22, 1991

[30] Foreign Application Priority Data

Mar. 24, 1990 [KR] Rep. of Korea ............... 90-3994
Dec. 29, 1990 [KR] Rep. of Korea ............. 90-22332

[51] Int. Cl.$^5$ ............................................. C07D 501/18
[52] U.S. Cl. ........................................ 540/226; 540/227
[58] Field of Search .............. 540/226, 227; 514/206, 514/208

[56] References Cited

FOREIGN PATENT DOCUMENTS 0397511 11/1990 European Pat. Off. .

Primary Examiner—Nicholas S. Rizzo
Attorney, Agent, or Firm—Ladas & Parry

[57] ABSTRACT

The present invention provides certain novel cephalosporin derivatives represented by following formula(I), which are especially useful as intermediates for the preparation of cephalosporin compounds possessed with potent and broad antibacterial activities.

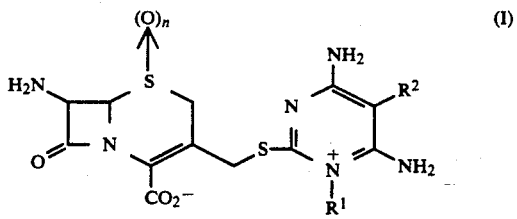

wherein:
$R^1$ is a $C_{1-4}$alkyl, $C_{3-4}$alkenyl, $C_{3-4}$cycloalkyl, amino optionally substituted with a $C_{1-4}$ alkyl radical, or phenyl group optionally substituted on its 2-, 4- and/or 6-position with a halogen, $C_{1-4}$ alkyl, $C_{1-3}$ alkoxy or hydroxy radical;
$R^2$ is hydrogen or a $C_{1-4}$ alkyl group; and
n is either 0 or 1.

The invention also relates to processes for preparing these intermediates and their pharmacologically active cephalosporin antibiotics.

4 Claims, No Drawings

CEPHALOSPORIN INTERMEDIATES

FIELD OF THE INVENTION

The present invention relates to certain novel cephalosporin derivatives, which are especially useful as intermediates for the preparation of certain cephalosporin compounds possessed with potent and broad antibacterial activities. The invention also relates to processes for preparing these intermediates and their pharmacologically active cephalosporin antibiotics.

DESCRIPTION OF THE PRIOR ART

Antibiotics of cephalosporin series are widely used in therapy for treatment of diseases which are caused by general pathogenic bacteria in human beings and animals. It has been known that such antibiotics are useful for the treatment of diseases caused by bacteria exhibiting the resistance to other antibiotics, e.g., penicillin-resistant bacteria, and for treatment of penicillin-sensitive patients.

In most circumstances, it is desirable to employ antibiotics showing broad antibacterial activities against both Gram-positive and Gram-negative bacteria. In this regard, there have been made many studies in developing a variety of cephalosporin antibiotics with broad-spectrum antibiotic activities.

Recently, the inventors of the present invention together with others have discovered that certain novel antibiotic cephalosporin compounds having the structural formula(A) as defined below and their derivatives, as disclosed in European Patent Application No. 397,511, have surprisingly superior antibiotic activity against a wide range of organisms:

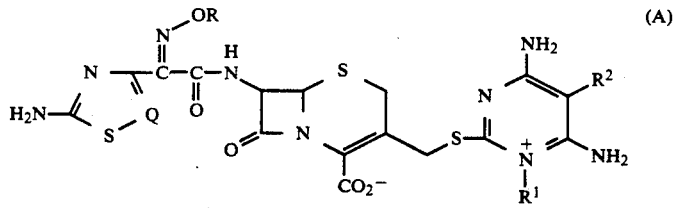

wherein:
R is a $C_{1-4}$ alkyl, $C_{3-4}$ alkenyl, $C_{3-4}$ alkynyl group, or $-C(R^a)(R^b)CO_2H$, wherein $R^a$ and $R^b$, which may be the same or different, are hydrogen or a $C_{1-4}$ alkyl group, or $R^a$ and $R^b$ form a $C_{3-7}$ cycloalkyl group with the carbon atom to which they are linked;

$R^1$ is a $C_{1-4}$ alkyl, $C_{3-4}$ alkenyl, $C_{3-7}$ cycloalkyl, amino optionally substituted with a $C_{1-4}$ alkyl radical, phenyl, or 2-, 4- or 6-substituted phenyl group with two or fewer substituents chosen from $C_{1-4}$ alkyl, $C_{1-3}$ alkoxy, halogen and hydroxy radicals;

$R^2$ is hydrogen or a $C_{1-4}$ alkyl group; and Q is N or CH.

In European Patent Application No. 397,511, it is disclosed that the compounds of formula(A) are synthesized by reacting the compounds of formula(B) with the compounds of formula(III) as illustrated below:

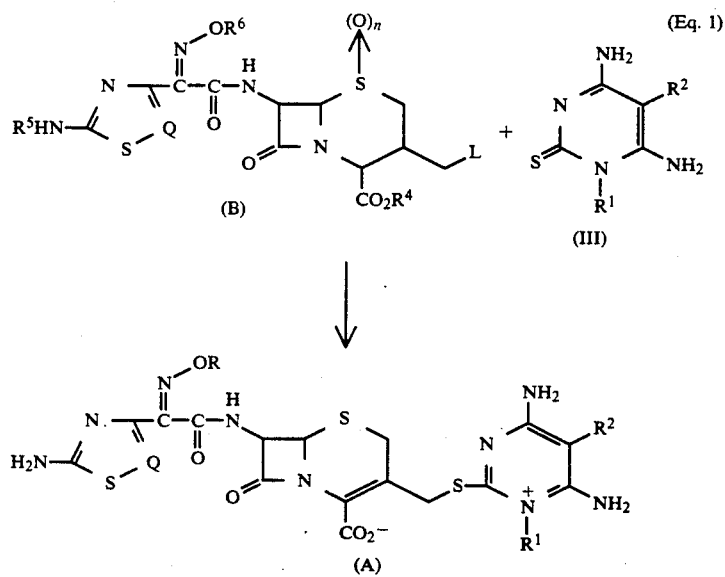

wherein:
$R^1$, $R^2$, R and Q have the same meanings as defined before;
n is either 0 or 1;
$R^4$ is hydrogen or a carboxyl-protecting group;
$R^5$ is hydrogen or an amino-protecting group;
$R^6$ is a $C_{1-4}$ alkyl, $C_{3-4}$ alkenyl or $C_{3-4}$ alkynyl group or $-C(R^a)(R^b)CO_2(R^c)$, wherein $R^a$ and $R^b$, which may be the same or different, are a hydrogen atom or a $C_{1-4}$ alkyl group, or $R^a$ and $R^b$ may form a $C_{3-7}$ cycloalkyl group with the carbon atom to which they are linked, and $R^c$ is hydrogen or a carboxyl-protecting group; and L is a leaving group.

The starting compounds of formula(B) mentioned above are well known as intermediates employed for the preparation of cephalosporin compounds. The above substitution (Eq. 1) is normally conducted in an aqueous solution at an elevated temperature, e.g., 60°–80° C. However, it suffers from the critical defect of producing undesirable by-products stemming from, e.g., the destruction of the β-lactam ring. These by-products not only lower the purity and yield of the final product; but also make it much more difficult to separate and purify the end product(A). Most importantly, these deficiencies make the overall manufacturing process for cephalosporin compounds(A) less economical owing to the fact that the compounds directly affected are the most expensive end product.

SUMMARY OF THE INVENTION

In accordance with the present invention, it has been discovered that the employment of novel compounds of formula(I) described below as the starting material for the preparation of pharmaceutically effective cephalosporin compounds, e.g., those compounds having the structure of formula(A), as fully described in European Patent Application No. 397,511 which is incorporated herein by reference, substantially cures or remedies all of the deficiencies associated with the previously known process such as (Eq. 1).

Accordingly, a primary objective of the present invention is to provide novel cephalosporin intermediates of formula(I), which may be employed for the synthesis of, among other things, those cephalosporin compounds defined by formula(A).

The cephalosporin intermediates according to the present invention may be represented as:

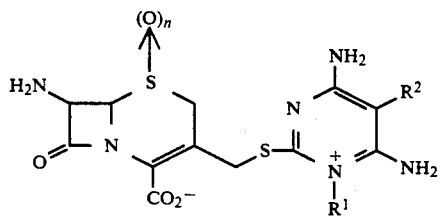

wherein:

$R^1$ is a $C_{1-4}$ alkyl, $C_{3-4}$ alkenyl, $C_{3-4}$ cycloalkyl, amino optionally substituted with a $C_{1-4}$ alkyl radical, or phenyl group optionally substituted on its 2-, 4- and/or 6-position with a halogen, $C_{1-4}$ alkyl, $C_{1-3}$ alkoxy or hydroxy radical;

$R^2$ is hydrogen or a $C_{1-4}$ alkyl group; and
n is either 0 or 1.

Another aspect of the present invention resides in the process of preparing a compound of formula(A), which comprises reacting the intermediate of formula(I) with a thiazole or thiadiazole derivative of formula(IV) defined below:

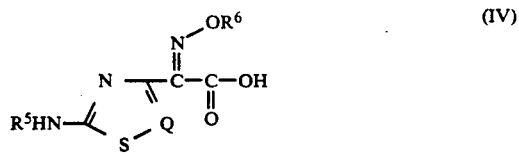

wherein:

$R^6$ and Q have the same meanings as defined previously; and $R^5$ is hydrogen or an amino-protecting group.

A further aspect of the present invention involves a process for preparing the compound of formula(I), which comprises reacting a cephem derivative of formula(II) with a pyrimidinethione compound of formula(III):

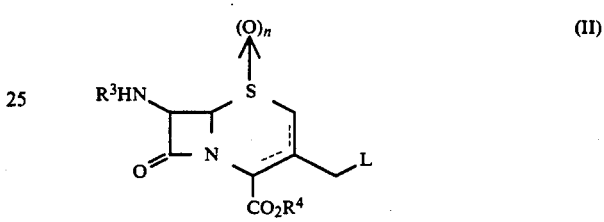

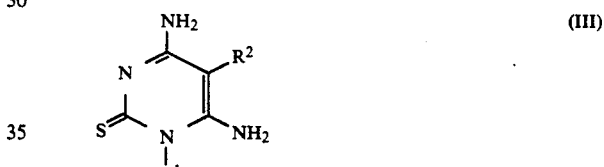

wherein:

$R^1$ and $R^2$ have the same meanings as defined in formula(I);

$R^3$ is hydrogen or an amino-protecting group;

$R^4$ is hydrogen or a carboxyl-protecting group;

L is a leaving group; and n is 0 or 1.

DETAILED DESCRIPTION OF THE INVENTION

The novel compounds of formula(I) according to the present invention may include their resonance isomers of formulas(I)′ and (I)″:

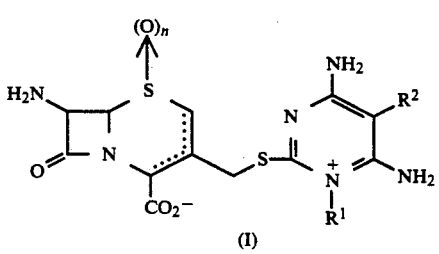

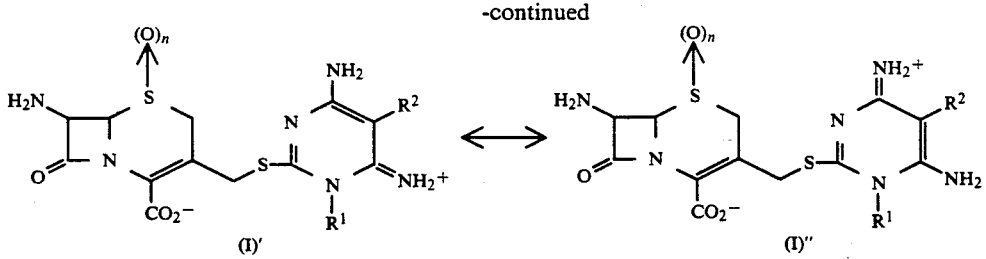

More preferred compounds of formula(I) in accordance with the present invention are those: wherein $R^1$ is a $C_{1-4}$ alkyl, $C_{3-4}$ alkenyl or amino group; and $R^2$ is hydrogen or a $C_{1-2}$ alkyl group.

Most preferred compounds of formula(I) in accordance with the present invention are those: wherein $R^1$ is a methyl, ethyl or amino group; and $R^2$ is hydrogen or a methyl group.

The specific intermediates of particular interest include:

7-amino-3-(4,6-diamino-1-methyl-pyrimidinium-2-yl)thiomethyl-3-cephem-4-carboxylate; 7-amino-3-(4,6-diamino-1-ethylpyrimidinium-2-yl)thiomethyl-3-cephem-4-carboxylate; 7-amino-3-(1,4,6-triaminopyrimidinium-2-yl)thiomethyl-3-cephem-4-carboxylate; 7-amino-3-(4,6-diamino-1,5-dimethylpyrimidinium-2-yl)thiomethyl-3-cephem-4-carboxylate; and 7-amino-3-(5-methyl-1,4,6-triaminopyrimidinium-2-yl)thiomethyl-3-cephem-4-carboxylate.

The novel intermediate compound of formula(I) can be effectively employed to produce, e.g., a cephalosporin compound of formula(A) by way of reacting said compound of formula(I) with a thiazole or thiadiazole derivative of formula(IV) as follows:

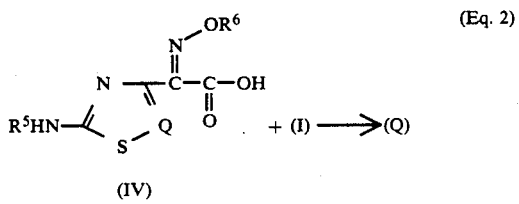

wherein: $R^5$, $R^6$ and Q have the same meanings as defined in (Eq. 1).

The above reaction represented by (Eq. 2) may be carried out in two steps: a condensation process; and a deprotection process or a process of removing the amino-protecting group and/or the carboxyl-protecting group as needs be.

The condensation process is normally conducted in the presence of an organic solvent and preferably together with an organic base at a temperature ranging from $-50°$ to $30°$ C., more preferably, from $-30°$ to $10°$ C.

Representative organic solvents which may be employed in the condensation reaction include: N,N-dimethylacetamide, dimethylformamide, acetone, acetonitrile, tetrahydrofuran, dioxane and dimethylsulfoxide; and, more preferably, N,N-dimethylacetamide and dimethylformamide.

Some of the organic bases which may be effectively used in the reaction are: triethylamine, pyridine and N,N-dimethylaniline; and, triethylamine is more preferred.

The end product of formula(A) obtained from the reaction represented by (Eq. 2) is of a sufficiently high degree of purity for normal application; however, if a higher purity is desired, the final product may be further purified by employing an ion exchange chromatography or by washing, i.e., dissolving and precipitating the product in an aqueous medium through controlling the pH from the two separate ranges where said dissolution takes place, i.e., either from the first range between 1 and about 2.5, or from the second range between 7 and 8 to the pH range where said precipitation occurs, i.e., between 3 and 4.5.

The novel compound of formula(I) is prepared by coupling a cephem compound of formula(II) with a pyrimidinethione compound of formula(III) as follows:

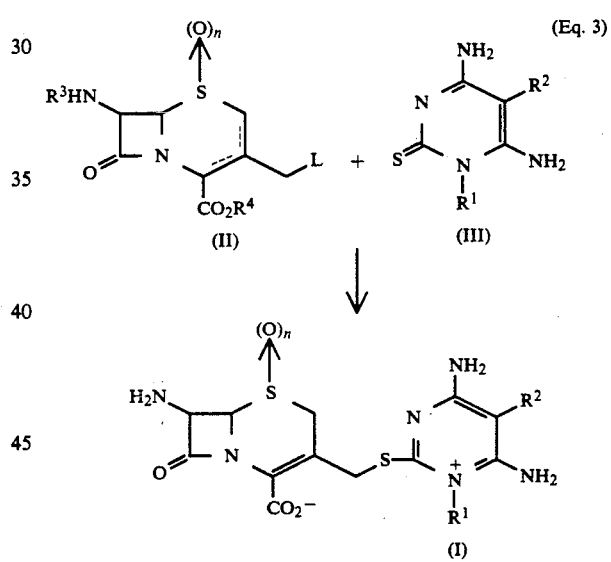

wherein: $R^1$, $R^2$, $R^3$, $R^4$, L and n have the same respective meanings as previously defined.

In formula(II) above, the dotted line represents a single and/or double bond. That is, the compounds of formula(II) used herein, unless specifically otherwise indicated, should be understood to represent compounds of either formula(II-a) or (II-b), or a mixture thereof, as described below;

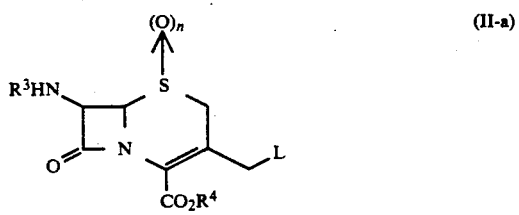

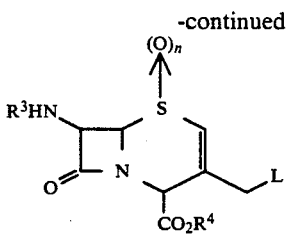

$$\text{(II-b)}$$

The reaction represented by (Eq. 3) above may be carried out either in an aqueous medium such as water or a mixture of water and water-miscible solvent; or more advantageously, in an organic solvent, and preferably in the presence of, e.g., a boron trifluoride solvate.

In the reaction carried out in an aqueous system to produce the compound of formula(I), the pH of the reaction solution is preferably controlled within a range from 5 to 8, more preferably, from 6 to 7.5; and the temperature is preferably maintained within a range from 40° to 100° C., more preferably, from 60° to 80 C.

In this reaction, the compound of formula(III) is used preferably in an amount of from 1 to 2 molar equivalents based on the compound of formula(II).

To stabilize the aqueous reaction process of (Eq. 3), one or more salts selected from the group consisting of sodium iodide, potassium iodide, sodium bromide, potassium bromide and potassium thiocyanate can be effectively used as a stabilizing agent.

Alternatively, and more preferably, the reaction process of (Eq. 3) may be effectively carried out in an organic solvent preferably in the presence of, e.g., a boron trifluoride solvate at a temperature ranging from −20° to 50° C., more preferably, from 20° to 50° C.; and for a period from about 30 minutes to 10 hours, more preferably, from 30 minutes to 5 hours.

The organic reaction process has a number of advantages over the aqueous reaction process such as: a lower level of impurities or by-products produced, higher yield, and easier to further purify the product(I), if desired.

In this organic process, the compound of formula (III) is used in an amount of from 0.5 to 2 molar equivalents, and preferably from 0.8 to 1.2 molar equivalents, based on the compound of formula(II).

The organic solvents, which may be employed in the reaction in an amount ranging from 2 to 20ml, more preferably, from 5 to 10ml per 1 gram of the compound-(II), may include: ethers(e.g., diethyl ether, dioxane, tetrahydrofuran, anisole), nitriles(e.g., acetonitrile, propionitrile), halogenated hydrocarbons(e.g., methylene chloride, chloroform, 1,2-dichloroethane), and mixtures of at least two of the foregoing; and, more preferably, ethers and nitriles.

The boron trifluoride solvates, which may be preferably used in an amount of from 0.5 to 10 molar equivalents, more preferably, from 2 to 5 equivalensts, based on the compounds of formula(II), may include those with dialkyl ethers(e.g., diethyl ether, diisopropyl ether) and those with nitriles(e.g., acetonirile, propionitrile); and, more preferably, boron trifluoride diethyl ether.

As stated above, the compound of formula(I) obtained from the organic reaction process can be effectively separated and purified by employing a conventional method such as recrystallization, column chromatography over silica gel or ion-exchange column or by washing with an aqueous solution through adjusting pH from the range where said dissolution takes place, i.e., either from the range between 1 and about 2.5 or from the range between 7 and 8 to the range where said precipitation occurs, i.e., between 3 and 4.5 with an acid such as hydrochloric acid, sulfuric acid and phosphoric acid or a base such as aqueous ammonia solution, alkali metal hydroxide, alkali metal phosphate and alkali metal hydrogen carbonate.

The amino-protecting group($R^5$ in formula(B) of (Eq. 1) and in formula(IV) of (Eq. 2), and $R^3$ in formula(II) of (Eq. 3)) may include: an acyl, substituted or unsubstituted aryl(lower)alkyl(e.g., benzyl, diphenylmethyl, triphenylmethyl and 4-methoxybenzyl), halo(lower)alkyl(e.g., trichloromethyl and trichloroethyl), tetrahydropyranyl, substituted phenylthio, substituted alkyliedene, substituted aralkylidene or substituted cycloalkylidene group. The acyl group used as an amino protecting group may include, for example, a $C_{1-6}$ (lower)alkanoyl(e.g., formyl and acetyl), $C_{2-6}$ alkoxycarbonyl-(e.g., methoxycarbonyl and ethoxycarbonyl) group, wherein the acyl group can be substituted with 1-3 substituent(s) such as halogen, hydroxy, cyano or nitro. In addition, the amino protecting group may include reaction products obtained from an amino group and a silane, boron or phosphorus compound.

The carboxyl or acid protecting group ($R^c$ in formula(B) of (Eq. 1) and in formula(IV) of (Eq. 2) and $R^4$ in formula(II) of (Eq. 3)) may include: (lower)alkylesters(e.g., methylester and t-butylester), (lower)alkenylesters(e.g., vinylester and allylester), (lower)alkoxy (lower)alkylesters(e.g., methoxymethylester), (lower)alkylthio(lower)alkylesters(e.g., methylthiomethylester), halo(lower)alkylesters(e.g., 2,2,2-trichloroethylester), substituted or unsubstituted aralkylesters (e.g., benzylester and p-nitrobenzylester) and silylesters.

The leaving group L(in formula(B) of (Eq. 1) and in formula(II) of (Eq. 3)) may include: a halogen such as chloride, bromide, fluoride or iodide, a (lower)alkanoyloxy group such as acetoxy, a (lower)alkanesulfonyloxy group such as methanesulfonyloxy, an arylsulfonyloxy group such as p-toluenesulfonyloxy, an alkoxycarbonyloxy group and the like.

The term "lower" as used hereinabove and elsewhere in this specification, for example, in reference to "lower alkyl," encompasses compounds having 1 to 6 carbon atoms, more preferably, 1 to 4 carbon atoms.

Amino or acid protecting groups can be readily removed from the product obtained either in (Eq. 1), (Eq. 2) or (Eq. 3) by any of the conventional deprotection methods which are well known in the field of cephalosporin art. For example, acid- or base-hydrolysis or reduction is generally applicable. For further example, when the protecting group is an amido group, it is feasible to subject such protected compounds to iminohalogenation and imino-etherification, followed by hydrolysis. Acid hydrolysis is preferred to remove such groups as tri(di)phenylmethyl or alkoxycarbonyl; and may be carried out in the presence of an organic acid such as formic acid, trifluoroacetic acid or p-toluenecetic acid, or an inorganic acid such as hydrochloric acid and the like.

Reduction of S-oxide may be carried out by adding potassium iodide and acetylchloride, followed by quenching with sodium m-bisulfite.

The following examples illustrate how some of the compounds of formula(I), i.e., Examples 1 to 10, and formula(A), i.e., Examples 11 to 42, can be prepared in accordance with the preferred embodiments of the present invention.

EXAMPLE 1

Synthesis of 7-amino-3-(4,6-diamino-1-methyl-pyrimidinium-2-yl)thiomethyl-3-cephem-4-carboxylate Under an anhydrous condition, a solution containing 2.72 g of 3-acetoxymethyl-7-amino-3-cephem-4-carboxylic acid and 1.56 g of 4,6-diamino-1-methyl-2-(1H)pyrimidinethione suspended in 20 ml of dry acetonitrile was cooled to 0° C.; and 3.6 ml of boron trifluoride diethylether was added. The temperature of the reaction solution was increased to a room temperature, e.g., 18°-20° C.; the solution was stirred for three hours; and then 10 ml of methyl alcohol was added. The resultant solution was stirred for 10 minutes and was added with 30 ml of ice water. The pH of the solution was adjusted to 7.1 by adding aqueous ammonia solution After concentration under a reduced pressure, e.g., about 20 mmHg, the solution was adjusted to pH 3.7 with 2N-aqueous hydrochloric acid; and allowed to stand at a room temperature for 24 hrs. The precipitates resulted from the reaction solution were filtered, washed with 10 ml of distilled water and with 10 ml of methyl alcohol, and dried to give 2.69 g of the title compound as a solid.

Yield: 73%

NMR: $\delta$(DMSO d-6): 2.13(broad s, 2H), 3.35(ABq, 2H), 3.48(s, 3H), 4.31 (ABq, 2H), 4.53(d, 1H), 4.81(d, 1H), 5.52(s, 1H), 7.5~8.4(broad d, 4H)

EXAMPLE 2

Synthesis of 7-amino-3-(4,6-diamino-1-ethylpyrimidinium-2-yl)thiomethyl-3-cephem-4-carboxylate Under an anhydrous condition, a solution containing 2.72 g of 3-acetoxymethyl-7-amino-3cephem-4-carboxylic acid and 1.8 g of 4,6-diamino-1-ethyl-2-(1H)-pyrimidinethione suspended in 20 ml of dry dioxane was cooled to 0° C.; and 3 ml of boron trifluoride diethylether was added. The temperature of the reaction solution was increased to 40° C.; the solution was stirred for one hour; and then 10 ml of methyl alcohol was added. The resultant solution was stirred for 10 minutes and was added with 30 ml of ice water. The pH of the solution was adjusted to 7.1 by adding aqueous ammonia solution After concentration under a reduced pressure, e.g., about 20 mmHg, the solution was adjusted to pH 3.6 with 2N-aqueous hydrochloric acid; and allowed to stand at a room temperature for 24 hrs. The precipitates resulted from the reaction solution were filtered, washed with 10 ml of distilled water and with 10 ml of methyl alcohol, and dried to give 2.87 g of the title compound as a solid.

Yield: 75%

NMR: $\delta$(DMSO d-6): 1.23(t, 2H), 3.37(ABq, 2H), 4.05(q, 2H), 4.31(ABq, 2H), 4.53(d, 1H), 4.78(d, 1H), 5.55(s, 1H), 7.8~8.1 (broad d, 4H)

EXAMPLE 3

Synthesis of 7-amino-3-(1,4,6-triaminopyrimidinium-2-yl)thiomethyl-3-cephem-4-carboxylate Under an anhydrous condition, a solution containing 2.72 g of 3-acetoxymethyl-7-amino-3-cephem-4-carboxylic acid and 1.50 g of 1,4,6-triamino-2(1H)-pyrimidinethione suspended in 20 ml of dry acetonitrile was cooled to 0° C.; and 4.8 ml of boron trifluoride diethylether was added. The temperature of the reaction solution was increased to 50° C; the solution was stirred for two hours; and then 10 ml of methyl alcohol was added. The resultant solution was stirred for 10 minutes and was added with 30 ml of ice water. The pH of the solution was adjusted to 7.1 by adding aqueous ammonia solution. After concentration under a reduced pressure, e.g., about 20 mmHg, the solution was adjusted to pH 3.7 with 2N-aqueous hydrochloric acid; and allowed to stand at a room temperature for 24 hrs. The precipitates resulted from the reaction solution were filtered, washed with 10 ml of distilled water and with 10 ml of methyl alcohol, and dried to give 2.55 g of the title compound as a solid.

Yield: 69%

NMR: $\delta$(DMSO d-6): 3.31(ABq, 2H), 4.01(ABq, 2H), 4.55(d, 1H), 4.78(d, 1H), 5.48(s, 1H), 6.17(s, 2H), 7.6-8.2(broad d, 4H)

EXAMPLE 4

Synthesis of 7-amino-3-(4,6-diamino-1,5-dimethyl-pyrimidinium-2-yl)thiomethyl-3-cephem-4-carboxylate Under an anhydrous condition, a solution containing 2.72 g of 3-acetoxymethyl-7-amino-3-cephem-4-carboxylic acid and 1.70 g of 4,6-diamino-1,5-dimethyl-2-(1H)-pyrimidinethione suspended in a mixture of 10 ml of dry acetonitrile and 10 ml of dioxane was cooled to 0° C.; and 4.8 ml of boron trifluoride diethylether was added. The temperature of the reaction solution was increased to 50° C.; the solution was stirred for five hours; and then 10 ml of methyl alcohol was added. The resultant solution was stirred for 10 minutes and was added with 30 ml of ice water. The pH of the solution was adjusted to 7.1 by adding aqueous ammonia solution After concentration under a reduced pressure, e.g., about 20 mmHg, the solution was adjusted to pH 3.7 with 2N-aqueous hydrochloric acid; and allowed to stand at a room temperature for 24 hrs. The precipitates resulted from the reaction solution were filtered, washed with 10 ml of distilled water and with 10 ml of methyl alcohol, and dried to give 3.02 g of the title compound as a solid.

Yield: 79%

NMR: $\delta$(DMSO d-6): 1.87(s, 3H), 3.38(ABq, 2H), 3.49(s, 3H), 4.28(ABq, 2H), 4.52(d, 1H), 4.79(d, 1H), 7.5-7.8(broad d, 4H)

The following compounds of Examples 5 to 10 were synthesized in a similar manner as was employed in Examples 1 to 4.

EXAMPLE 5

Synthesis of 7-amino-3-(5-methyl-1,4,6-triaminopyrimidinium-2-yl)thiomethyl-3-cephem-4-carboxylate Yield: 73%

NMR: $\delta$(DMSO d-6): 1.86(s, 3H), 3.33(ABq, 2H), 4.12(ABq, 2H), 4.52(d, 1H), 4.77(d, 1H), 6.07(s, 2H), 7.60.8.20(broad d, 4H)

EXAMPLE 6

Synthesis of 7-amino-3-(4,6-diamino-1-methyl-5-ethylpyrimidinium-2-yl)thiomethyl-3-cephem-4-carboxylate Yield: 77%

NMR: δ(DMSO d-6): 0.90(t, 3H), 2.37(q, 2H), 3.33(ABq, 2H), 3.48(s, 3H), 4 27(ABq, 1H), 4.50(d, 1H), 4.76(d, 1H), 7.5~7.8 (broad d, 4H)

EXAMPLE 7

Synthesis of 7-amino-3-(4,6-diamino-5-methyl-1-ethylpyrimidinium-2-yl)thiomethyl-3-cephem-4-carboxylate Yield: 71%

NMR: δ(DMSO d-6): 1.22(t, 3H), 1.81(s, 3H), 3.32(ABq, 2H), 4.04(q, 2H), 4.27(ABq, 1H), 4.52(d, 1H), 4.76(d, 1H), 7.3~7.8 (broad d, 4H)

EXAMPLE 8

Synthesis of 7-amino-3-(4,6-diamino-1,5-diethylpyrimidinium-2-yl)thiomethyl-3-cephem-4-carboxylate Yield: 68%

NMR: δ(DMSO d-6): 0.94(t, 3H), 1.21(t, 3H), 2.36(q, 2H), 3.34(ABq, 2H), 4.08(q, 2H), 4.27(ABq, 1H), 4.52(d, 1H), 4.72(d, 1H), 7.2~7.8(broad d, 4H)

EXAMPLE 9

Synthesis of 7-amino-3-(4,6-diamino-1-propylpyrimidinium-2-yl)thiomethyl-3-cephem-4-carboxylate Yield: 73%

NMR: δ(DMSO d-6): 0.92(t, 3H), 1.65(m, 2H), 3.34(ABq, 2H), 3.88(t, 2H), 4.3(ABq, 2H), 4.52(d, 1H), 4.78(d, 1H), 5.50(s, 1H), 7.6-8.1(board d, 4H)

EXAMPLE 10

Synthesis of 7-amino-3-(4,6-diamino-1-(4-hydroxyphenyl)-pyrimidinium-2-yl)thiomethyl-3-cephem-4-carboxylate Yield: 65%

NMR: δ(DMSO d-6): 3.27(ABq, 2H), 4.18(ABq, 2H), 4.52(d, 1H), 4.77(d, 1H), 5.58(s, 1H), 6.87 7.21(m, 4H), 8.01 8.21(broad d, 4H)

The novel cephalosporin intermediates synthesized in Examples 1 to 10 are further summarized in Table 1 hereof.

TABLE 1

Cephalosporin Intermediates Synthesized in Examples 1 to 10 (n = 0)

(I)

| Example Nos. | $R^1$ | $R^2$ |
|---|---|---|
| 1 | —$CH_3$ | H |
| 2 | —$CH_2CH_3$ | H |
| 3 | —$NH_2$ | H |
| 4 | —$CH_3$ | —$CH_3$ |

TABLE 1-continued

Cephalosporin Intermediates Synthesized in Examples 1 to 10 (n = 0)

(I)

| Example Nos. | $R^1$ | $R^2$ |
|---|---|---|
| 5 | —$NH_2$ | —$CH_3$ |
| 6 | —$CH_3$ | —$CH_2CH_3$ |
| 7 | —$CH_2CH_3$ | —$CH_3$ |
| 8 | —$CH_2CH_3$ | —$CH_2CH_3$ |
| 9 | —$CH_2CH_2CH_3$ | H |
| 10 | 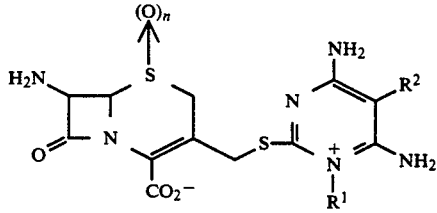 | H |

EXAMPLE 11

Synthesis of 7-[(z)-2-(2-aminothiazol-4-yl)-2-methoxyimino)acetamido]-3-(4,6-diamino-1-methylpyrimidinium-2-yl)thiomethyl-3-cephem-4-carboxylate A solution containing 4.44 g of (z)-2-(methoxyimino)-2-[2-(triphenylmethyl)aminothiazol-4-yl]acetic acid dissolved in 20 ml of N,N-dimethylacetamide was cooled to 0° C. To the solution were added 6.1 ml of triethylamine and 2.20 g of mesitylene sulfonyl chloride; and the resultant was stirred for 20 minutes and further cooled to −20° C. 3.68 g of 7-amino-3-(4,6-diamino-1-methylpyrimidinium-2-yl)thiomethyl-3-cephem-4-carboxylate (prepared in Example 1) was added. The reaction solution was stirred for one hour; and, after addition of 100 ml of distilled water, was adjusted to pH 3.5 with 1N aqueous hydrochloric acid. After stirring, the solid thus produced was filtered, washed with 20 ml of distilled water and 50 ml of acetone and dried in a vacuum to provide 7.11 g of protected cephem product. The protected product was dissolved in 30 ml of formic acid cooled to 0° C.; and the resultant solution was stirred at a room temperature for 2 hours. The solid thus produced was filtered and washed with 10 ml of formic acid. The filtrates were combined and concentrated under a reduced pressure, e.g., about 20 mmHg; and, after addition of 50 ml of methanol, stirred at a room temperature for 30 minutes. The insolubles were removed by filtration; and 300 ml of diethyl ether was added to the solution while stirring. The resultant solid was filtered, washed with 50 ml of acetone and dried in a vacuum to afford 4.55 g of the title compound Yield 82.5%; purity 98.7%

EXAMPLE 12

Synthesis of 7-(z)-2-(2-aminothiazole-4-yl)-2-(methoxyimino)acetamido]-3-(1,4,6-triaminopyrimidinium-2-yl)thiomethyl-3-cephem-4-carboxylate 4.37 g of the title compound was obtained in the same manner as described in Example 11, by employing 3.69 g of 7-amino-3-(1,4,6-triaminopyrimidinium-2-yl)thiomethyl-3-cephem-4-carboxylate(prepared in Example 3), instead. Yield: 79.1%; purity 99.1%

EXAMPLE 13

Synthesis of
7-[(z)-2-(2-aminothiazol-4-yl)-2-ethoxyimino)acetamido]-3-(4,6-diamino-1-methylpyrimidinium-2-yl)thiomethyl-3-cephem-4-carboxylate A solution containing 4.58 g of (z)-2-(ethoxy imino)-2-[2-(triphenylmethyl)aminothiazol-4-yl]acetic acid dissolved in 20 ml of N,N-dimethylacetamide was cooled to 0° C. To the solution were added 6.1 ml of triethylamine and 2.20 g of mesitylene sulfonyl chloride; and the resultant was stirred for 20 minutes and further cooled to −20° C. 3.68 g of 7-amino-3-(4,6-diamino-1-methylpyrimidinium-2-yl) thiomethyl-3-cephem-4-carboxylate(prepared in Example 1) was added. The reaction solution was stirred for one hour; and, after addition of 100 ml of distilled water, was adjusted to pH 3.5 with 1N aqueous hydrochloric acid. After stirring, the solid thus produced was filtered, washed with 20 ml of distilled water and 50 ml of acetone and dried in a vacuum to provide 7.30 g of protected cephem product. The protected product was dissolved in 30 ml of formic acid cooled to 0° C.; and the reaction solution was stirred at a room temperature for 2 hours The solid thus obtained was filtered and washed with 10 ml of formic acid. The filtrates were combined and concentrated under a reduced pressure, e.g., about 20 mmHg; and, after addition of 50 ml of methanol, stirred at a room temperature for 30 minutes. The insolubles were removed by filtration; and 300 ml of diethyl ether was added to the solution while stirring. The resultant solid was filtered, washed with 50 ml of acetone and dried in a vacuum to afford 4.73 g of the title compound.
Yield: 83.7%; purity: 98.7%

EXAMPLE 14

Synthesis of
7-[(z)-2-(2-aminothiazole-4-yl)-2-(methoxyimino)acetamido]-3-(1,4,6-triaminopyrimidinium-2-yl)thiomethyl-3-cephem-4-carboxylate 4.71 g of the title compound was obtained in the same manner as described in Example 13, by employing 3.69 g of 7-amino-3-(1,4,6-triaminopyrimidinium-2-yl) thiomethyl-3-cephem-4-carboxylate(prepared in Example 3). Yield: 83.2%; purity: 99.4%

EXAMPLE 15

Synthesis of
7-[(z)-2-(2-aminothiazol-4-yl)-2-(2-propyn-1-oxyimino)acetamido]-3-(4,6-diamino-1-methylpyrimidinium-2-yl)thiomethyl-3-cephem-4-carboxylate A solution containing 4.68 g of (z)-2-(2-propyn-1-oxyimino)-2-[2-(triphenylmethyl)amiothiazol-4-yl]acetic acid dissolved in 20 ml of N,N-dimethylacetamide was cooled to 0° C. To the solution were added 6.1 ml of triethylamine and 2.20 g of mesitylene sulfonyl chloride; and the resultant was stirred for 20 minutes and further cooled to −20° C. 3.68 g of 7-amino-3-(4,6-diamino-1-methylpyrimidinium-2-yl) thiomethyl-3-cephem-4-carboxylate(prepared in Example 1) was added. The reaction solution was stirred for one hour; and, after addition of 100 ml of distilled water, was adjusted to pH 3.5 with 1N aqueous hydrochloric acid. After stirring, the solid thus produced was filtered, washed with 20 ml of distilled water and 50 ml of acetone and dried in a vacuum to provide 7.17 g of protected cephem product. The protected product was dissolved in 30 ml of formic acid cooled to 0° C.; and the reaction solution was stirred at a room temperature for 2 hours The solid thus obtained was filtered and washed with 10 ml of formic acid. The filtrates were combined and concentrated under a reduced pressure; and, after addition of 50 ml of methanol, stirred at a room temperature for 30 minutes. The insolubles were removed by filtration; and 300 ml of diethyl ether was added to the solution while stirring. The resultant solid was filtered, washed with 50 ml of acetone and dried in a vacuum to afford 4.81 g of the title compound Yield: 83.6%; purity 98.9%

EXAMPLE 16

Synthesis of
7-[(z)-2-(2-aminothiazole-4-yl)-2-(2-propyn-1-oxyimino)acetamido]-3-(4,6-diamino-1-ethylpyrimidinium-2-yl)thiomethyl-3-cephem-4-carboxylate 4.79 g of the title compound was obtained in the same manner as described in Example 15, by employing 3.82 g of 7-amino-3-(4,6-diamino-1-ethylpyrimidinium-2-yl)thiomethyl-3-cephem-4-carboxylate(prepared in Example 2). Yield: 80.3%; purity: 99.3%

EXAMPLE 17

Synthesis of
7-[(z)-2-(2-aminothiazole-4-yl)-2-(2-propyn-1-oxyimino)acetamido]-3-(1,4,6-triaminopyrimidinium-2-yl)thiomethyl-3-cephem-4-carboxylate 4.90 g of the title compound was obtained in the same manner as described in Example 15, by employing 3.69 g of 7-amino-3-(1,4,6-triaminopyrimidinium-2-yl) thiomethyl-3-cephem-4-carboxylate(prepared in Example 3). Yield 85.0%; purity 98.1%

EXAMPLE 18

Synthesis of
7-[(z)-2-(2-aminothiazol-4-yl)-2-(2-carboxyprop-2-oxyimino)acetamido]-3-(4,6-diamino-1-methyl-pyrimidinium-2-yl)thiomethyl-3-cephem-4-carboxylate A solution containing 5.72 g of (z)-2-(2-t-butoxycarbonylprop-2-oxyimino)-2-[2-(triphenylmethyl) aminothiazol-4-yl]acetic acid dissolved in 20 ml of dimethylformamide was cooled to 4° C. To the solution were added 6.1 ml of triethylamine and 2.20 g of mesitylene sulfonyl chloride; and the resultant was stirred for 5 minutes and further cooled to −10° C. 3.68 g of 7-amino3-(4,6-diamino-1-methylpyrimidinium-2-yl)thiomethyl-3-cephem-4-carboxylate (prepared in Example 1) was added. The reaction solution was stirred for one hour; and, after addition of 100 ml of distilled water, was adjusted to pH 3.1 with 1N aqueous hydrochloric acid. After stirring, the solid thus produced was filtered, washed with 20 ml of distilled water and 50 ml of acetone and dried in a vacuum to provide 8.71 g of protected cephem product. The protected product was dissolved in a mixture of 30 ml of formic acid and 4.7 ml of concentrated hydrochloric acid cooled to 0° C.; and the reaction solution was stirred at a room temperature for 2 hours. The solid thus obtained was filtered and washed with 10 ml of formic acid. The filtrates were combined and concentrated under a reduced pressure and, after addition of 20 ml of methanol, stirred at a room temperature for 30 minutes. The insolubles were removed; and 300 ml of distilled water was added to the solution The pH was adjusted to 7 by adding saturated aqueous sodium bicarbonate solution. Methanol was removed under a reduced pressure and the resultant aqueous solution was adjusted to pH 3.1 with 1N aqueous hydrochloric acid and stirred at 4° C. The solid thus produced was filtered, washed successively with 10 ml of distilled water, 10 ml of acetone and 10 ml of methanol and dried in a vacuum to afford 5.29 g of the title compound. Yield: 84.9%; purity: 98.9%

EXAMPLE 19 to 42

The cephalosporin compounds 19 to 42 as contained in Table 2 hereof were prepared in a manner similar to those employed in Examples 11 to 18, using the intermediates prepared in Examples 1 to 10 and various thiazole- or thiadiazole-containing starting compounds, as shown in Table 2.

TABLE 2

Cephalosporin Antibiotics Synthesized in Examples 11 to 42 (A)

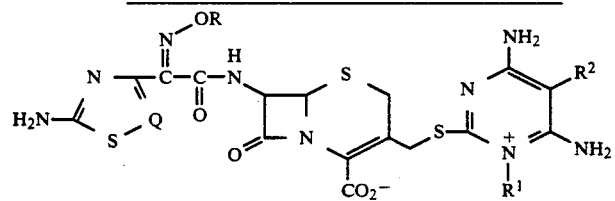

| Example Nos. | R | $R^1$ | $R^2$ | Q |
|---|---|---|---|---|
| 11 | —$CH_3$ | —$CH_3$ | H | CH |
| 12 | —$CH_3$ | —$NH_2$ | H | CH |
| 13 | —$CH_2CH_3$ | —$CH_3$ | H | CH |
| 14 | —$CH_2CH_3$ | —$NH_2$ | H | CH |
| 15 | —$CH_2C\equiv CH$ | —$CH_3$ | H | CH |
| 16 | —$CH_2C\equiv CH$ | —$CH_2CH_3$ | H | CH |
| 17 | —$CH_2C\equiv CH$ | —$NH_2$ | H | CH |
| 18 | $C(CH_3)_2CO_2H$ | —$CH_3$ | H | CH |
| 19 | —$CH_3$ | —$CH_2CH_3$ | H | CH |
| 20 | —$CH_3$ | —$NH_2$ | —$CH_3$ | CH |
| 21 | —$CH_2CH_3$ | —$CH_2CH_3$ | H | CH |
| 22 | —$CH_2CH_3$ | —$CH_3$ | H | N |
| 23 | —$CH_2CH_3$ | —$CH_2CH_3$ | H | N |
| 24 | —$CH_2CH_3$ | —$NH_2$ | H | N |
| 25 | —$CH_2CO_2H$ | —$CH_3$ | H | CH |
| 26 | —$CH_2CO_2H$ | —$CH_2CH_3$ | H | CH |
| 27 | —$CH_2CO_2H$ | —$NH_2$ | H | CH |
| 28 | —$CH(CH_3)CO_2H$ | —$CH_3$ | H | CH |
| 29 | —$CH(CH_3)CO_2H$ | —$CH_2CH_3$ | H | CH |
| 30 | —$CH(CH_3)CO_2H$ | —$CH_2CH_2CH_3$ | H | CH |
| 31 | —$CH(CH_3)CO_2H$ | —$NH_2$ | H | CH |
| 32 | —$CH(CH_3)CO_2H$ | —$NH_2$ | —$CH_3$ | CH |
| 33 | —$CH(CH_3)CO_2H$ | —$CH_3$ | —$CH_3$ | CH |
| 34 | —$C(CH_3)_2CO_2H$ | —$CH_2CH_3$ | H | CH |
| 35 | —$C(CH_3)_2CO_2H$ | —$CH_2CH_2CH_3$ | H | CH |
| 36 | —$C(CH_3)_2CO_2H$ | —$NH_2$ | H | CH |
| 37 | —$C(CH_3)_2CO_2H$ | —$NH_2$ | —$CH_3$ | CH |
| 38 | —$C(CH_3)_2CO_2H$ | —$CH_3$ | —$CH_3$ | CH |
| 39 | —$C(CH_3)_2CO_2H$ | —$CH_3$ | —$CH_2CH_3$ | CH |
| 40 | —$C(CH_3)_2CO_2H$ | —$CH_2CH_3$ | —$CH_3$ | CH |
| 41 | —$C(CH_3)_2CO_2H$ | —$CH_2CH_3$ | —$CH_2CH_3$ | CH |
| 42 | —$C(CH_3)_2CO_2H$ | 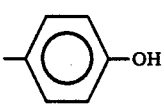 | H | CH |

As can be clearly seen from the above examples, novel cephalosporin intermediates of formula (I) can be efficiently produced in high degrees of yield and purity in accordance with the preferred reaction process of the present invention; and, furthermore, said intermediates of formula (I) can be effectively employed to produce such potent cephalosporin antibiotics of formula (A) in high yields and purities by carrying out the reaction in an organic medium in accordance with the novel process of the present invention.

We claim:

1. A cephalosporin intermediate represented by formula(I)

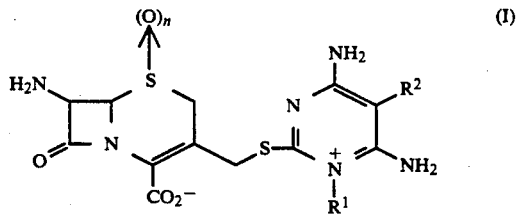

wherein:

$R^1$ is a $C_{1-4}$ alkyl, $C_{3-4}$ alkenyl, $C_{3-4}$ cycloalkyl, amino optionally substituted with a $C_{1-4}$ alkyl radical, or phenyl group optionally substituted on its 2-, 4- and/or 6-position with a halogen, $C_{1-4}$ alkyl, $C_{1-3}$ alkoxy or hydroxy radical;

$R^2$ is hydrogen or a $C_{1-4}$ alkyl group; and n is either 0 or 1.

2. The intermediate of claim 1, wherein:

$R^1$ is a $C_{1-4}$ alkyl, $C_{3-4}$ alkenyl or amino group; and $R^2$ is hydrogen or a $C_{1-2}$ alkyl group.

3. The intermediate of claim 2, wherein $R^1$ is a methyl, ethyl or amino group; and $R^2$ is hydrogen or a methyl group.

4. The intermediate of claim 3 which is selected from the group consisting of:

7-amino-3-(4,6-diamino-1-methylpyrimidinium-2-yl)thiomethyl-3-cephem-4-carboxylate;

7-amino-3-(4,6-diamino-1-ethylpyrimidinium-2-yl)thiomethyl-3-cephem-4-carboxylate;

7-amino-3-(1,4,6-triaminopyrimidinium-2-yl)thiomethyl-3-cephem-4-carboxylate;

7-amino-(4,6-diamino-1,5-dimethylpyrimidinium-2-yl)thiomethyl-3-cephem-4-carboxylate; and 7-amino-3-(5-methyl-1,4,6-triaminopyrimidinium-2-yl)thiomethyl-3-cephem-4-carboxylate.

* * * * *